United States Patent [19]
Zomorrodi et al.

[11] Patent Number: 4,550,254
[45] Date of Patent: Oct. 29, 1985

[54] LOW COST INFRARED REFLECTANCE DENSITOMETER SIGNAL PROCESSOR CHIP

[75] Inventors: Mehrdad Zomorrodi, Culver City; Li-Fung Cheung, Los Angeles; Simon M. L. Law, Torrance, all of Calif.

[73] Assignee: Xerox Corporation, Stamford, Conn.

[21] Appl. No.: 571,393

[22] Filed: Jan. 16, 1984

[51] Int. Cl.⁴ ............................................. G01J 1/00
[52] U.S. Cl. ................................ 250/338; 250/252.1; 355/3 DD
[58] Field of Search ............... 250/252.1, 338 R, 341; 315/291, 307; 355/3 DD, 14 D

[56] References Cited

U.S. PATENT DOCUMENTS

| | | | |
|---|---|---|---|
| 4,182,977 | 1/1980 | Stricklin, Jr. | 315/307 |
| 4,372,672 | 2/1983 | Pries | 355/3 DD |
| 4,377,338 | 3/1983 | Ernst | 355/3 DD |
| 4,451,135 | 5/1984 | Okumura | 355/3 DD |
| 4,462,680 | 7/1984 | Ikeda | 355/3 DD |
| 4,506,973 | 3/1985 | Ernst | 355/3 DD |

Primary Examiner—Janice A. Howell
Attorney, Agent, or Firm—Franklyn C. Weiss

[57] ABSTRACT

An integrated circuit chip with digital and analog circuits thereon for providing a low cost infrared reflectance densitometer for detecting relative toner density on a photoreceptive surface including several stages of calibration including photodiode detection means 208 for monitoring and controlling the light output from a light emitting diode 206, photodiode means 302 for detecting undesired scattered and reflected background light signals, further photodiode means 304 for detecting the light reflected from said photoreceptive surface as may be affected by toner deposited thereon, an automatic gain control circuit 400 for automatically adjusting the output gain of the reflectance densitometer, and sample and hold circuit means 600 for adjusting the circuit for different effects of the aging, leakage current effects, or other undesired performance characteristics of the circuit components.

11 Claims, 3 Drawing Figures

LOW COST INFRARED REFLECTANCE DENSITOMETER SIGNAL PROCESSOR CHIP

This invention relates to a low cost infrared reflectance densitometer on a single integrated circuit chip which permits the measurement of the relative optical density of developed toner on the photoreceptor of a printer or office copier which is used to control the process variables such as toner density and charge distribution.

BACKGROUND OF THE INVENTION

Office copiers and printers utilizing the xerographic process of toner development of a latent image on a photoreceptive surface, are becoming more sophisticated with the use of integrated and other type of high technology circuits. In addition, to increase the reliability of the copier or printer and to render as high quality an output document as possible, certain process variables such as toner density and charge distribution on the photoreceptor must be controlled. However, measurements of these factors can be misleading or false due to errors in optics, the optoelectronic chain, and certain environmental effects. Thus, it would be desirable to fabricate control circuitry to allow the measurement of the relative optical density of the developed toner and other parameters, but overcome the deleterious error effects as set forth above.

According to the present invention, an integrated circuit chip is provided with digital and analog circuits thereon for providing a low cost infrared reflectance densitometer for detecting relative toner density on a photoreceptive surface including several stages of calibration including photodiode detection means for monitoring and controlling the light output from a light emitting diode, photodiode means for detecting undesirable scattered background light signals, further photodiode means for detecting the light reflected from said photoreceptive surface as may be affected by toner deposited thereon, an automatic gain control circuit for automatically adjusting the output gain of the reflectance densitometer, and sample and hold circuit means to adjust the circuit for different effects of the aging, leakage current effects or other performance characteristics of the circuit components.

DESCRIPTION OF THE DRAWINGS

For a more complete understanding of the invention, reference may be had to the following detailed description of the invention in conjunction with the drawings wherein.

DETAILED DESCRIPTION OF THE INVENTION

As the speed of xerographic copiers and printers increases, that is, the number of copies per minute increases, the control of the toner concentration and the charge distribution on the photosensitive surface becomes increasingly important. One method of monitoring the toner density, developer bias, charging level, and other important process variables, is to sense the developed toner mass on the photoreceptor; then, depending upon this developed mass, the toner on the photoreceptor, the charging level, and other process variables in the printer or copier can be adjusted automatically by the circuit. One technique for monitoring the developed mass on the photoreceptor is to illuminate and develop on the drum or xerographic photoreceptive belt, for example, a small area called a patch and then monitor its developed toner mass, reflectance from the photoreceptive surface, etc.

Figure 1:
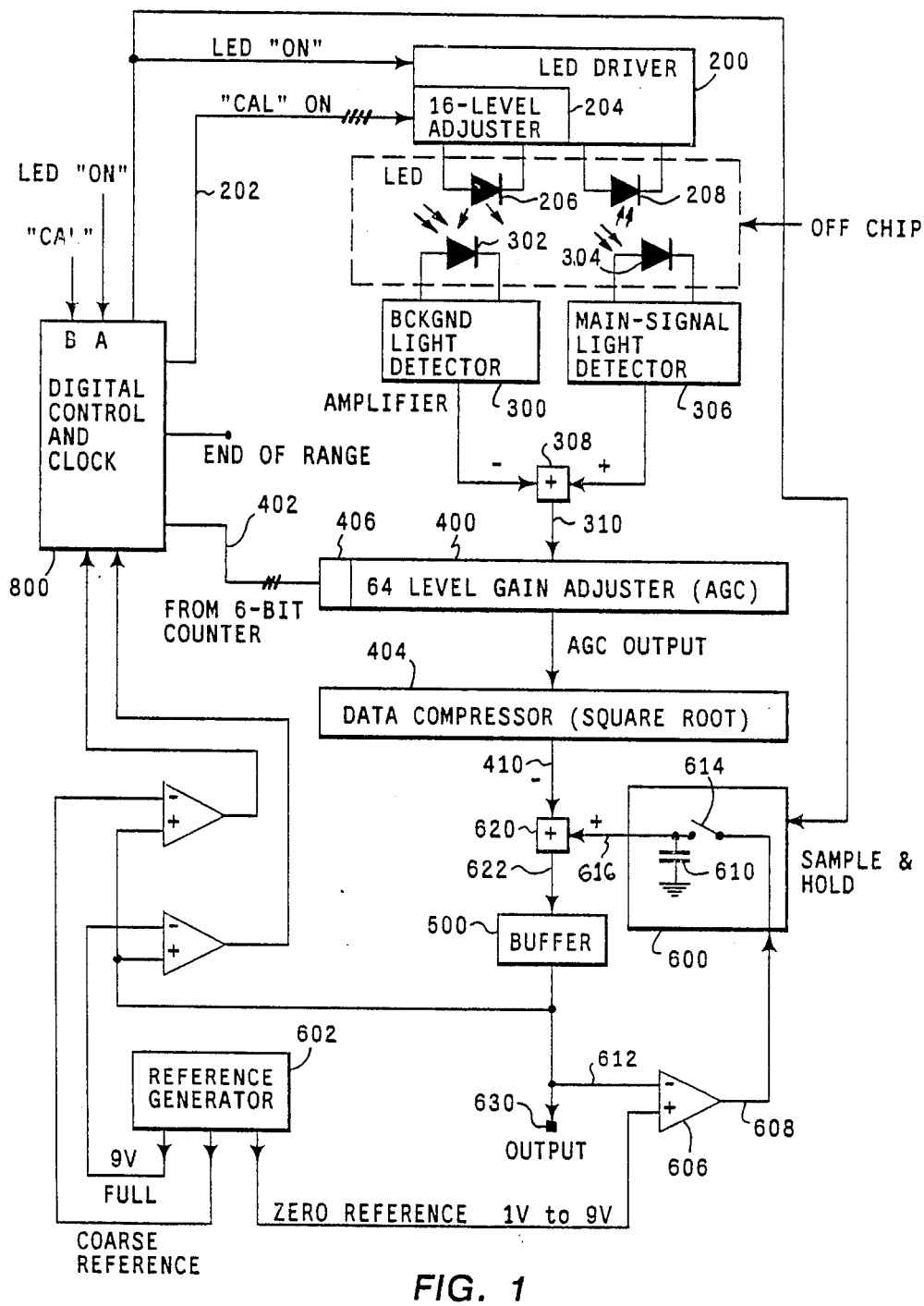
FIG. 1 is a block diagram of the infrared reflectance densitometer chip in accordance with the principles of the present invention.

FIG. 1 shows the logic section digital control and timer 800, comprising digital circuits which are responsive to control signals from an external source such as a microprocessor somewhere else in the system and used to monitor system operation. The input to the logic section comprises at least two signals, one of which is the LED "ON" signal and the other is the calibrate "ON" signal. The LED "ON" signal would be utilized when the circuitry is operational and monitoring the patch on the drum or belt or other photoconductive surface on a copy by copy basis. The calibrate "ON" signal would be triggered by the central microprocessor every periodic number of repetitions, such as, for example, for every 10,000 or so copies. That is, the system would be recalibrated on this periodic basis so as to maintain the accuracy of the reflectance densitometer of the present invention. In the calibrate "ON" position, a signal would be received from the logic section 800 on line 202 to the LED driver circuit 200. This initiates the calibration cycle which will be described as follows.

In the calibration mode, the patch area on the xerographic or photoconductive surface would not have any toner on it and thus the light being emitted by the LED 206 would be completely reflected to its maximum level. The 16 level adjuster 204 comprises a four bit digital to analog converter which is utilized to increase the light intensity of light emitting diode 206 in 16 level increments, the increment stops when the output 630 reaches coarse scale reference. If the 16th level of adjustment is reached, there are, of course, no more levels of adjustment and cleaning of optics or replacement of LED 206 must be made in order to allow for future adjustments of the light output. The photodiode 208 receives light directly from LED 206 and is utilized as a feedback to the LED driver 200 in order to maintain the light intensity of the LED 206 at a fixed level. If the radiant power of LED 206 drops, photodiode 208 will detect this decrease in light intensity, feed it back to the LED driver circuit 800 and increase the light intensity. Thus, the combination of LED 206 and photodiode 208 are utilized in conjunction with the 16 level adjustment circuit to maintain the output of LED 206 at a fixed level.

Figure 2:
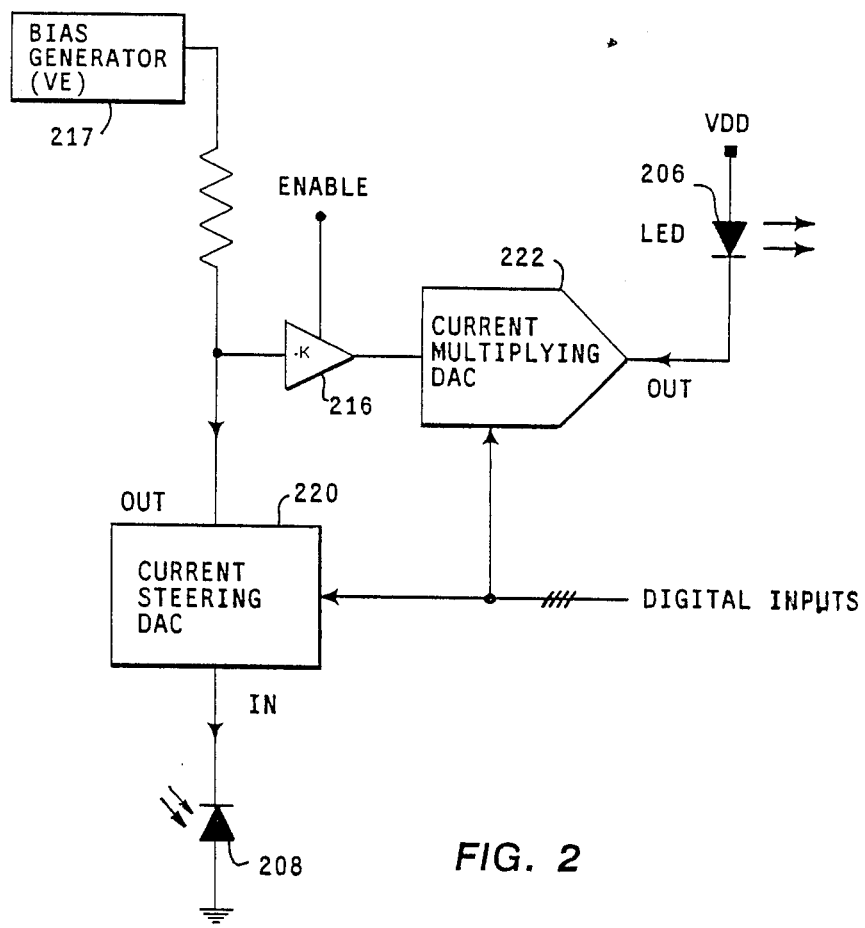
FIG. 2 is a schematic diagram of the LED driver as seen in FIG. 1.

FIG. 2 shows the components comprising LED driver circuit 200. This circuit, together with the optical feedback loop set forth above, maintains the radiant power of the LED 206 at a fixed level once the input digits to the circuit are set. This function is required because the radiant power of the LED is strongly dependent upon temperature and length of use. Once the enabling digits from the logic section are set, the single ended amplifier 216 tries to maintain the voltage on the input line to the amplifier 216 are established by bias generator 218. This is accomplished through the negative feedback provided by the LED 206 output and the photodiode 208 input to the current steering digital to analog converter 220. If photodiode 208 detects a decrease in output from light emitting diode 206, the current through the digital to analog converter 220 will be decreased, the voltage will be affected at amplifier 216 thereby changing the current flow through the current multiplying digital to analog converter 222 to increase the current flow through the light emitting diode 206, thereby increasing the light output therefrom. This adjustment of the LED 206, as from 10 milliamps to 100 milliamps in 16 discrete levels, is a coarse adjustment. There is no electrical connection between the light emitting diode 206 and the rest of the electronic circuits so the subsequent circuitry is utilized for fine calibration of the system.

The second part of calibration is done utilizing two other photodiodes 302 and 304. Photodiode 302 receives light inside the apparatus that may be scattered from other components as radiated by LED 206. This light, which would be reflected from other surfaces than the photoreceptor, is undesired and thus photodiode 302 is located in such a place to capture only this background light which is used to be subtracted from the signal from the main signal light detector 306. Photodiode 304 receives the signal reflected from the patch selected on the photoreceptive surface but includes all the background light which is not desired. Background light detector 300 passes its signal representative of the undesirable light to the subtractor circuit 308. Main signal light detector 306 passes the output from photodiode 304 to the subtractor circuit 308, but this signal includes, as set forth above, all the reflected light both background and from the desired patch. If the background light is subtracted from the main signal light, then the signal remaining will be the desired reflected signal from the patch, which is the desired signal to be passed on to further circuitry to be discussed below.

Figure 3:
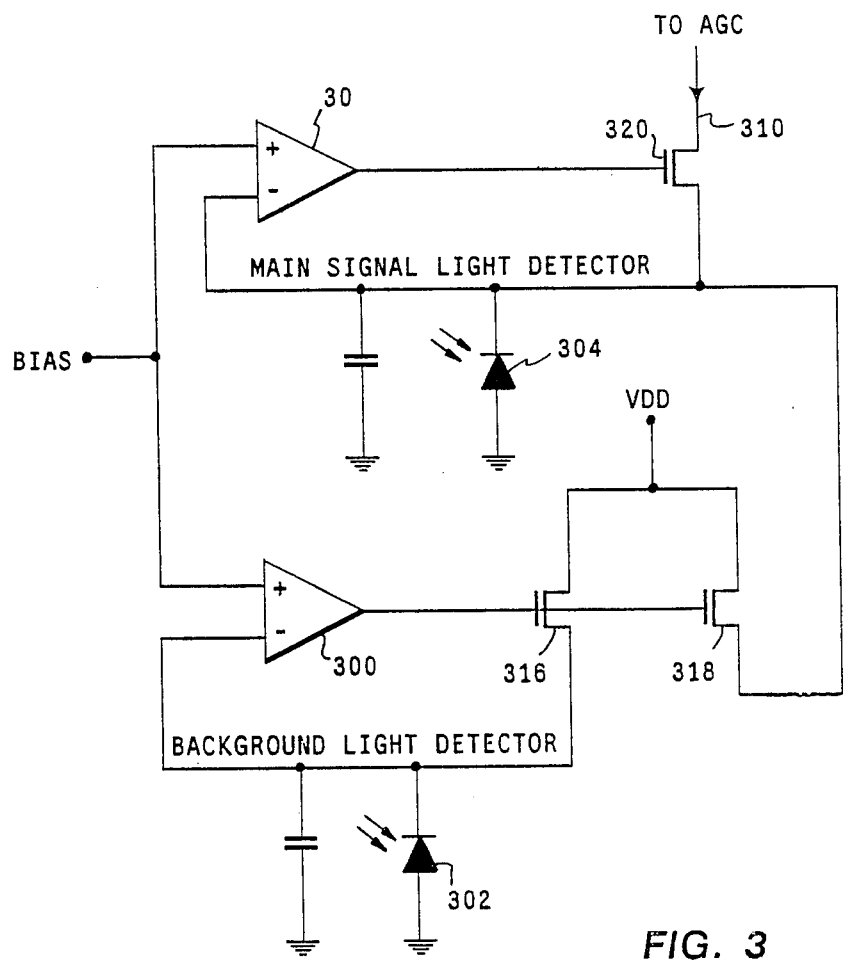
FIG. 3 is a schematic diagram of the background and main light detectors as seen in FIG. 1.

FIG. 3 shows the circuits utilized for the background light detector 300 and the main signal light detector 306. The input bias to the FIG. 3 is used to bias the photodiodes 302 and 304 at their respective reverse bias voltages since photodiodes should work in a reverse bias mode. That is, they give the reverse bias current proportional to light, so they must be biased at some higher voltage so that the anode with respect to the cathode would be negative in the reverse bias mode. Differential amplifiers 300 and 306 force the same bias voltage applied to it at the other input node so that by biasing the positive input of the amplifiers 300 and 306, the inverting input of the amplifiers is forced to the same voltage because of the high gain of the amplifier. The feedback is made in order to get the current to the output 310 to the rest of the circuit. The feedback is just like a source output 310 to the rest of the circuit. The feedback is just like a source follower transistor. This feedback makes the cathode of the photodiodes a very low impedance node. A low impedance node is desired at this point because it is desired to extract the current out of it when there is no load on it. When there is no light on the photodiodes, there is a current through them called leakage current. The amplifier 300 is utilized for background light subtraction as the background light is a very small current. It is a small current because the background light is a very low intensity light and thus that current must be highly amplified in order to be utilizeable by the rest of the circuit. Utilizing the current mirror technique, by keeping the gate to source voltages of the two transistors 316, 318 equal, the voltage output is the same. So gate to source voltage of one transistor is equal to gate to source voltage of the other transistor, however transistor 320 is much larger than transistors 316, 318 so the current which flows represents a predetermined amount of background light current. The current output goes to the AGC circuit and is the main signal light minus the background light at the output node.

As the circuit in FIG. 1 compensates for any degradation of light or reduction in gain due to dirt contamination, and other mechanical mounting problems, belt fluttering, and temperature, calibration must be made on a bare patch with no toner deposited thereon. Thus, when the circuit is operating properly, the signal on line 310 comprises the full scale calibration signal which is presented to the 64 level gain adjuster circuit 400 indicative of the light from the bare patch on the photoreceptive surface. Of course, when the circuit is in the operational mode, the signal output from comparator 308 on line 310 will be the light detected from a test patch with toner during the normal operational cycle, but this signal can be used to compare with the bare patch signal in order to adjust the other operating parameters of the system as set forth above. The signal on line 310 is utilized to increase the gain of the 64 level gain adjuster circuit AGC 400 in 64 steps utilizing a 6 bit counter.

The AGC circuit 400 has a current to voltage converter and a 6 bit digital to analog converter which indicates current in, voltage out, and has a 6 bit digital to analog converter 406. This is utilized for gain adjustment and the voltage output from automatic gain control 400 is presented to data compression circuit 404. The gain of the AGC circuit 400 is controlled by a 6 bit digital counter in the logic section 800, with this signal on line 402 being converted to an analog level in a digital to analog converter 406. The data compressor circuit 404 is used to increase the dynamic range of the output signal. That is, by compressing the data from the input to the output of the data compressor circuit, there is a larger variation of the input. Thus, given the same swing at the output, there can be accommodated for more variation of the current at the input, allowing for more variation of the light at the input, that is, larger reflectivity range at the input. This allows for different reflectivities from different types of photoconductors and photoreceptors that may be used from machine to machine or from different types of machine to another type of machine. The circuit could comprise MOS transistors, switches, and analog switches with the square root circuit 404 comprising further MOS transistors in a typical prior art manner. While the LED driver 200 and background light detectors 300 and main signal light detector 306 are used for increasing the light output from the LED, the gain control circuit 400 and data compressor circuit 404 are utilized so that the electrical gain is increased such that the output from the data compressor circuit on line 410 reaches full scale for a bare patch on the photoreceptive surface.

At this point, the calibration part of the invention is complete and all the gains are now fixed until the next calibration period; for example, every 10,000 or so copies depending upon the system utilized. Thus, to reiterate, the first part of the calibration mode is to increase the gain of the LED 206 by means of photodiode 208 to maintain the LED radiant output at a fixed predetermined level (coarse adjustment). The second part of the calibration is to subtract any part of the background scattered light that may be detected at the photodiodes 302, 304 at areas on the photoreceptive surface that are not part of the patch. The third part of the calibration cycle is the increasing of the gain of the automatic gain control circuit 400 utilized with the data compression circuit 404 to increase the electrical output therefrom to full scale (fine adjustment).

There is part of the present invention a calibration step which is performed every cycle as opposed to every 10,000 or so cycles for the calibration mode set forth above. This calibration is termed the auto-zero cancellation mode. This auto-zero cancellation mode is utilized to offset any effects of changing electronic factors of the chip, the electronic factors of the circuit on the chip, and offset due to leakage of the photodiodes in the reflectance densitometer system. All photodiodes are different, as are the effects of fabrication between one integrated circuit and another, and while the components age, the effects thereof must be compensated for. The sample and hold circuit 600 is utilized for closing the loop and forcing the output of the circuit to zero reference when there is no light. That is, if LED 206 is extinguished, the light output from the circuit should be at a zero reference level thereby eliminating the effects of offset, drift, leakage, etc. If these effects are not eliminated, the output signal will not be accurate and will continue to change as the circuit ages and the adjustment by subsequent circuits of toner levels, charge distribution, etc., will not be as accurate as if all these effects are compensated for. As the sample and hold circuit 600 is utilized during both calibration and the normal reading mode of the system during operation of the circuit, it is operational during the period the LED "ON" signal is presented to the circuit. Reference generator 602 has at one of its outputs a zero reference voltage which could be one volt depending upon the circuit. This signal on line 604 is presented to high gain differential stage 606 which compares the voltage presented on line 604 with the voltage presented on the output line 612 of the circuit of which this application is the invention. The output of differential stage 606 is presented to sample and hold circuit 600 via line 608. If the switch 614 in the sample and hold circuit is closed, with the LED "ON" signal in the off state, capacitor 610 is charged to the output level of high gain differential stage 606. When the LED "ON" signal is applied to the circuit and thus to sample and hold circuit 600, the switch 614 is opened. Thus, when the signal is operational, that is, the LED "ON" signal is applied, switch 614 is opened and then the voltage on capacitor 610 is applied on line 616 to the input to adder 620. Thus, the differential stage 606 in the loop forces the output 630 to zero reference when thee is no trigger signal and the analog switch 614 of sample and hold circuit 600 is closed and the capacitor 610 is memorizing this voltage which corresponds to any offset voltage. Thus, during both calibration and during normal reading, that is, operation of the circuit, switch 614 becomes open. Thus, any time the sensor circuit herein is triggered, no matter if it is in the calibration or normal reading mode, the sample and hold switch 614 opens. Thus, the signal from square root circuit 404 is presented on line 410 to adder circuit 620. The output on line 622 is thus the zero reference voltage plus the main signal and is presented to buffer 500. The input to adder 620 is the main signal plus offset from the data compressor circuit 404, but the offset voltage gets subtracted in adder circuit 620, with the output being proportional to the main signal plus zero reference voltage.

The buffer circuit 500 now has applied to it on line 622 the main signal, amplifies and buffers it to condition the main signal for use by other circuits in the system to adjust the toner density, charge distribution, etc.

While the invention has been described with reference to specific embodiments, it will be understood by those skilled in the art that various changes may be made and equivalents may be substituted for elements thereof without departing from the true spirit and scope of the invention. In addition, many modifications may be made without departing from the essential teachings of the invention.

We claim:

1. An infrared reflectance densitometer for detecting relative toner density on a photoreceptive surface comprising:
    infrared light emitting diode means (206) for emitting light toward said surface,
    first photodiode detection means (208) adjacent said light emitting diode means and positioned for receiving, monitoring and controlling the direct light output therefrom,
    second photodiode detection means (302) adjacent said light emitting diode means and positioned for receiving and detecting only the scattered and reflected light from the background, excluding said surface,
    third photodiode detection means (304) adjacent said light emitting diode means and positioned for receiving and detecting only the light reflected from said surface as may be affected by toner deposited thereon,
    automatic gain control circuit means (400) for receiving the outputs from said second and third photodiode detection means for automatically generating an output signal (630) representative of the toner density on said photoreceptor surface, and
    sample and hold circuit means (600) for adjusting for the effects of aging and leakage current on the circuit components on said densitometer.

2. The densitometer as set forth in claim 1
    further including digital control logic means 800 which enables said densitometer to operate in a calibrate or normal operation mode, said calibrate mode being selected on a regular periodic basis upon control of an externally applied control signal, and
    LED driver circuit means (200) for supplying power to said light emitting diode means (206), said driver circuit means including a multi-level adjuster circuit means (204) which is enabled in said calibrate mode, said multi-level adjuster circuit means (204) comprising digital to analog converter circuit means (220, 222) and utilized to increase the power in said LED driver circuit means (200) to said light emitting diode means (206) in discrete multi-level increments until a coarse output level is reached.

3. The densitometer as set forth in claim 1 wherein said first photodiode detection means (208) detects said light from said light emitting diode means (206) and feeds this signal back to said LED driver circuit means (200) in order to maintain the light intensity from said light emitting diode means (206) at a fixed level.

4. The densitometer as set forth in claim 2 wherein said LED driver circuit means (200) comprises
    current multiplying digital to analog circuit means (222) for supplying operating current to said light emitting diode means (206),
    single-ended amplifier means (216), the output of which is coupled to the input of said current multiplying digital to analog converter (222), said single ended amplifier means (216) operating to maintain its input at a voltage potential established by a bias generator (217), and current steering amplifier means (220) coupled to the input to single ended amplifier means (216) and said first photodiode detection means (208), the current flowing through said amplifier means (220) decreasing as the current flowing through said first photodiode detection means (208) decreases, such that said single ended amplifier means (216) increases the current flow therethrough to increase the current multiplied in said current multiplying digital to analog circuit means (222) to increase the current through said light emitting diode means (206) to thereby increase its radiant power.

5. The densitometer as set forth in claim 4 further including background light detector means (300) coupled to said second photodiode detection means (302) for amplifying the light signal therefrom, and main signal light detector means (306) coupled to said third photodiode detection means (304) for amplifying the light signal therefrom.

6. The densitometer as set forth in claim 5 wherein said background light detector means (302) comprises a first differential amplifier means (300) for receiving the light signal from said background light detector means (302), first output transistor means (316, 318) for amplifying the output of said differential amplifier means 300, and wherein said main signal light detector means (306) comprises a second differential amplifier means (307) for receiving the light signal from said main signal light detector means (306), and second output transistor means (320) for amplifying the output of said differential amplifier means (307), such that the current that flows through said first output transistor means (316, 318) is substracted from the current that flows through second output transistor means (320), thereby eliminating the effects of background light from the main signal light.

7. The densitometer as set forth in claim 6 wherein said automatic gain control circuit means (400) receives the main light signal from said second output transistor means (320), said automatic gain control circuit means (400) comprises digital to analog converter means 406 for converting an input digital control signal in, and current to voltage converter means for providing a fine multi-level adjustment to the output current from said main signal light detector 306, and further comprising data compressor circuit means (404) for increasing the dynamic range of the output signal from said automatic gain control circuit means 400.

8. The densitometer as set forth in claim 3 further including subtraction circuit means 308 for subtracting the backgrond light signal from said second photodiode detection means (302) from the main light signal from said third photodiode detection means (304) to eliminate the effects of background light from the main light signal, and said automatic gain control means receiving said main light signal to increase the output signal therefrom on discrete multi-level increments until a fine output level is reached.

9. The densitometer as set forth in claim 7 wherein said sample and hold circuit means (600) is utilized to force the main light signal output to a zero reference when said light emitting diode means radiates no light, said sample and hold circuit means comprising high gain differential circuit means (606) coupled to compare a zero reference signal to said main light signal, switch means (614) coupled to said high gain differential circuit means (606) and the output from said automatic gain control means, and capacitor means (610) coupled to the output of said switch means (614), such that when said switch means (614) is closed, said capacitor means (610) charged to the zero reference reference as generated by said differential circuit means (606) and when said switch means (614) is open, the voltage on said capacitor means (610) is applied to the output of said automatic gain control circuit means (400), and further including adder circuit means (620) to add the main light signal from said automatic gain control circuit means to the zero reference voltage signal from same and hold circuit means (600).

10. Light emitting driver circuit means for maintaining constant the radiant light from a light emitting diode (206) as detected by a photodiode detector (208) comprising:

current multiplying digital to analog circuit means (222) for supplying operating current to said light emitting diode (206), bias generator (217) for generating a bias voltage, single ended amplifier means (216), the output of which is coupled to the input of said current multiplying digital to analog circuit means (222), said single ended amplifier means (216) operating to maintain its input at said bias voltage, and current steering amplifier means (220) coupled to the input to single ended amplifier means (216) and said first photodiode detection means (208), the current flowing through said amplifier means (220) decreasing as the current flowing through said first photodiode detection means (208) decreases, such that said single ended amplifier means (216) increases the current flow therethrough to increase the current multiplied in said current multiplying digital to analog circuit means (222) to increase the current through said light emitting diode means (206) to thereby increase its radiant power.

11. A circuit for eliminating the effects of background illuminated by a light emitting diode including a first light detector means (302) for detecting the background level of light and a second light detector means (304) for detecting the level of light reflected from a predetermined surface, comprising:

first differential amplifier means (300) for receiving the light signal from said first light detector means (302), first output transistor means (316, 318) for amplifying the output from said differential amplifier means (300), second differential amplifier means (307) for receiving the light signal from said second light detector means (304), second output transistor means (320) for amplifying the output of second differential amplifier means (307), such that the current that flows through said first output transistor means (316, 318) is subtracted from the current that flows through second output transistor means (320) to eliminate the effects of background light from the light reflected from said predetermined surface.

* * * * *